United States Patent [19]

Horiuchi et al.

[11] Patent Number: 4,960,701
[45] Date of Patent: Oct. 2, 1990

[54] N-ACETYLMANNOSAMINE DEHYDROGENASE, PROCESS FOR ITS PRODUCTION, METHOD FOR QUANTITATIVELY ANALYZING N-ACETYLMANNOSAMINE OR SIALIC ACID, AND KIT FOR THE QUANTITATIVE ANALYSIS

[75] Inventors: Tatsuo Horiuchi; Toshiko Kurokawa, both of Noda, Japan

[73] Assignee: Noda Institute for Scientific Research, Chiba, Japan

[21] Appl. No.: 121,916

[22] Filed: Nov. 17, 1987

[30] Foreign Application Priority Data

| Dec. 4, 1986 [JP] | Japan | 61-287843 |
| Dec. 12, 1986 [JP] | Japan | 61-294711 |
| Dec. 12, 1986 [JP] | Japan | 61-294712 |

[51] Int. Cl.$^5$ .................................................. C12N 9/04
[52] U.S. Cl. ....................................... 435/190; 435/850
[58] Field of Search ................................. 435/190, 850

[56] References Cited

FOREIGN PATENT DOCUMENTS

1336694A2  3/1985  European Pat. Off. .
60-184399  9/1985  Japan .

OTHER PUBLICATIONS

Yoneyama et al., "Distribution of Mannosamine and Mannosaminuronic Acid Among Cell Walls of Bacillus Species," J. Bacterial., vol. 149, No. 1, pp. 15–21, 1982.

De–Buch: H. U. Bergmeyer, Methods of Enzymatic Analysis, vol. VI, Verlag Chemie, Weinheim 1984, S. 80 bis 90.

Patent Abstracts of Japan C-351, Jun. 5, 1986, vol. 10/No. 15: 61–12299 (A).

Patents Abstracts of Japan C-327, Feb. 6, 1986, vol. 10/No. 3: 60–184 399 (A).

*Methods in Enzymology* (1963), vol. VI, pp. 465–467.

*Clinica Chimica Acta*, International Journal of Clinical Chemistry, vol. 108/1 (1980).

*Primary Examiner*—Robert A. Wax
*Attorney, Agent, or Firm*—Banner, Birch, McKie & Beckett

[57] ABSTRACT

N-Acetylmannosamine dehydrogenase which takes off hydrogen from N-acetylmannosamine to convert it into N-acetylmannosaminolactone and, at the same time, reduces coenzyme NAD into NADH. This enzyme can be obtained by culturing, in a medium, a strain belonging to Genus Flavobacterium and having an ability to produce N-acetylmannosamine dehydrogenase producing activity, and then collecting it. This enzyme is usable in the quantitative analysis of N-acetylmannosamine or sialic acid.

4 Claims, 4 Drawing Sheets

N-ACETYLMANNOSAMINE DEHYDROGENASE, PROCESS FOR ITS PRODUCTION, METHOD FOR QUANTITATIVELY ANALYZING N-ACETYLMANNOSAMINE OR SIALIC ACID, AND KIT FOR THE QUANTITATIVE ANALYSIS

BACKGROUND OF THE INVENTION

1. Field of the Invention

The present invention relates to novel N-acetylmannosamine dehydrogenase (hereinafter referred to as N-AMDH) which acts upon N-acetylmannosamine (hereinafter referred to as N-AM) to convert it into N-acetylmannosaminolactone and, at the same time, reduces nicotinamide adenine dinucleotide (NAD) into reduced nicotinamide adenine dinucleotide (NADH), as well as to a process for producing N-AMDH, an enzymatic method for quantitatively analyzing N-AM or sialic acid (hereinafter referred to as SA), and a kit for the quantitative analysis.

2. Description of the Prior Art

In the current clinical tests, SA in serum is measured, and this plays an important role in the diagnoses of acute and chronic inflammations, shocks, trauma, myocardial infarction, diabetes mellitus, liver diseases, cancers, etc.

The measurements of SA are roughly classified into chemical method and enzymatic method.

The chemical method is being gradually replaced by the enzymatic method of higher accuracy, because chemical method is inferior in various points such as specificity, workability, dangerousness of the agents used in its, etc.

Until today, method A and method B have been proposed as the enzymatic method, according to a rough classification.

Methods A and B are identical in that neuraminic acid aldolase is reacted upon SA to decompose the latter into N-AM and pyruvic acid. However, they are different from each other in that according to method A, N-AM is treated with acylglucosamine-2-epimerase and N-acetylhexosamine oxidase to form hydrogen peroxide and the latter is analyzed, while according to method B, pyruvic acid is treated with pyruvic acid oxidase or lactic acid dehydrogenase (LDH) to form hydrogen peroxide or NADH, respectively, and they are analyzed.

Method A is disadvantageous in that the existence of acylglucosamine-2-epimerase complicates the system, and method B is disadvantageous in that it is influenced by the endogenous pyruvic acid.

SUMMARY OF THE INVENTION

The present inventors studied a measurement of SA which is easy to operate and has a high accuracy. As the result, it was found that a bacterial strain belonging to Genus Flavobacterium isolated from the soil produces a novel enzyme which, when reacted with N-AM, converts the latter into N-acetylmannosaminolactone and, at the same time, reduces NAD into NADH, and this enzyme is effectively utilizable in the measurement of SA. Based on this finding, the present invention was accomplished.

Thus, the present invention provides a novel enzyme N-AMDH which, when reacted with N-AM, converts the latter into N-acetylmannosaminolactone and, at the same time, reduces NAD into NADH. Further, the invention also provides a process for producing N-AMDH which comprises culturing a strain belonging to Genus Flavobacterium and having an ability to produce N-AMDH in a medium and collecting N-AMDH from the cultured product. Further, the invention also provides a method for quantitatively analyzing N-AM which comprises treating an N-AM-containing sample with N-AMDH and determining the resulting NADH. Further, the invention also provides a method for quantitatively analyzing SA which comprises treating an SA-containing sample successively or simultaneously with N-acetylneuraminic acid aldolase and N-AMDH and determining the resulting NADH. Further, the invention also provides a quantitative analysis kit comprising at least N-AMDH, NAD and a buffer solution.

BRIEF DESCRIPTION OF THE DRAWINGS

In the accompanying drawings.

DETAILED DESCRIPTION OF THE INVENTION

Next, the present invention will be explained below more concretely.

Physico-chemical properties of the novel enzyme N-AMDH used in the present invention are as follows.

(1) Action and substrate-specificity

As shown in the following reaction scheme, N-AMDH oxidizes N-AM into N-acetylmannosaminolactone and, at the same time, reduces NAD into NADH in the presence of N-AM and NAD.

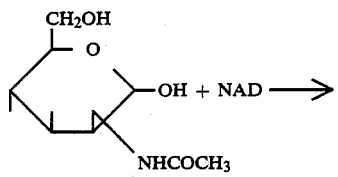

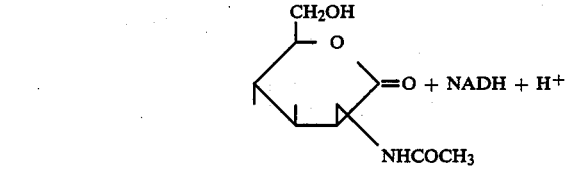

In the presence of water, N-acetylmannosaminolactone is spontaneously hydrolyzed to form N-acetylmannosaminic acid. Accordingly, the reaction is substantially irreversible. N-AMDH hardly acts or does not act at all upon other neutral sugars, hexosamine, N-acetylglucosamine and N-acetylgalactosamine, except that it acts upon N-glycolylmannosamine in the same manner as above. It hardly utilizes nicotinamide adenine dinucleotide phosphate (NADP), 2,6-dichlorophenol indophenol and the like as electron acceptor.

(2) Optimum pH and stable pH range

Its optimum pH is 8.0 to 9.0, when tris-hydrochloric acid buffer is used.

Figure 1:
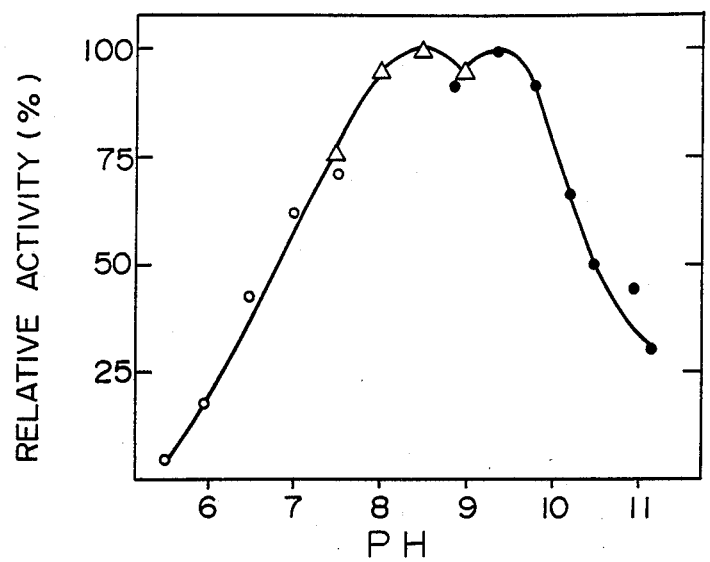
FIG. 1 is a graph illustrating the optimum pH value of this enzyme.

FIG. 1 illustrates the results of enzymatic activity measurement using potassium phosphate buffer, tris-hydrochloric acid buffer and glucine-sodium hydroxide buffer.

Figure 2:
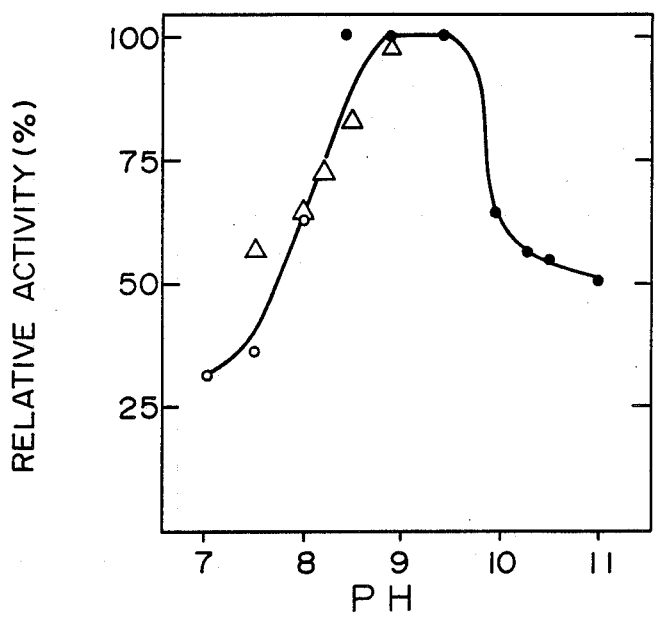
FIG. 2 is a graph illustrating its stable pH range.

As shown in FIG. 2, its stable pH range is 8.5 to 9.5.

The buffer solutions used there are potassium phosphate buffer, tris-hydrochloric acid buffer and glycine-sodium hydroxide buffer.

(3) Temperature range suitable for its action

Figure 3:
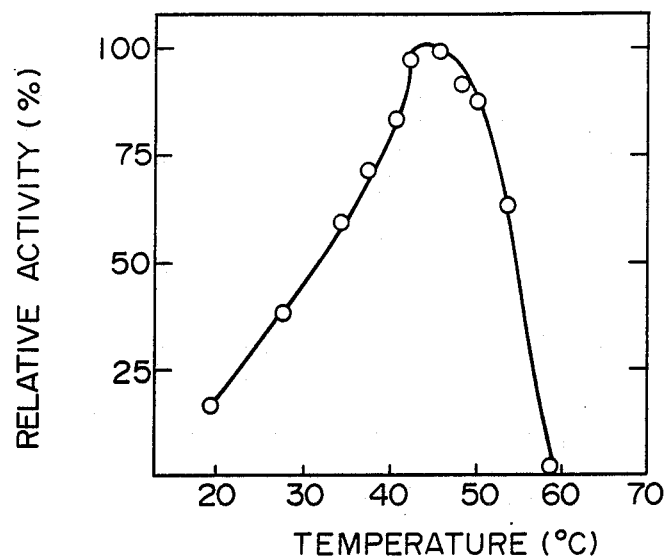
FIG. 3 is a graph illustrating the temperature range suitable for the action of this enzyme.

As shown in FIG. 3, it is 35° C. to 50° C.

(4) Conditions (pH, temperature) of inactivation

Figure 4:
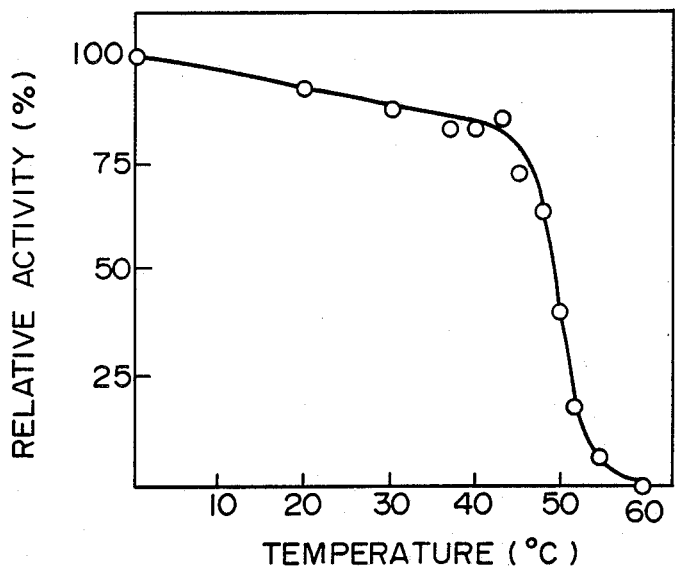
FIG. 4 is a graph illustrating the heat stability of this enzyme.

As shown in FIG. 4, it keeps activity at stable up to a temperature of 45° C., when heat treated for 10 minutes. At temperatures exceeding 45° C., it rapidly loses its activity. When heat treated at 45° C. for 10 minutes, it is stable at a pH of 8.5–9.5, while it is particularly instable at a pH value of 7 or below.

(5) Influence of inhibitor and stabilization

| Inhibitor | Residual activity (%) |
|---|---|
| None | 100 |
| $HgCl_2$ | 6 |
| $NiSO_4$ | 69 |
| $ZnSO_4$ | 71 |
| $CuSO_4$ | 79 |
| $NaN_3$ | 83 |
| SDS | 18 |
| KCN | 101 |
| EDTA | 89 |
| BSA | 96 |
| PCMB | 95 |
| Iodoacetamide | 87 |
| 8-Hydroxyquinoline | 95 |
| o-Phenanthroline | 87 |
| $\alpha,\alpha'$-Dipyridyl | 97 |
| 5'-AMP | 76 |

The table presented above illustrates the enzymatic activity of N-AMDH measured in solutions containing various metallic ions and inhibitors at a concentration of 2 mM. There is known no substance making a particular contribution to its activation and stabilization.

(6) Method of purification

This enzyme can be isolated and purified according to usual purifiying means such as column chromatography using DEAE-cellulose, precipitation using ammonium sulfate, column chromatography using DEAE-Sephadex, column chromatography using 5'-AMP-Sepharose, gel filtration using Sephadex, and the like, or combinations thereof.

(7) Molecular weight

As measured by gel filtration method using 0.05M tris-hydrochloric acid buffer (containing 0.1M NaCl) and Sephadex G-200 column, its molecular weight is about 110,000 to 120,000.

(8) Electrophoresis using polyacrylamide gel

Figure 5:
FIG. 5 is a diagram illustrating the electrophoretic band.

As shown in FIG. 5, acrylamide disk electrophoresis using 7.5% polyacrylamide gel gives a nearly single band. The migration distance after 80 minutes at 4 mA is 28 mm.

(9) Isoelectric point

As measured by acrylamide gel isoelectric focusing, its isoelectric point is 4.9.

(10) Activity measurement

To 1.8 ml of 0.05M tris-hydrochloric acid buffer (pH 8.2) is added 0.1 ml of 60 mM NAD solution. After keeping the mixture at 37° C. for 10 minutes, 10 microliters of enzyme solution is added, and then 0.1 ml of 0.3M N-AM is added. By homogenizing the mixture, the reaction is started. The reaction mixture is immediately transferred into a light absorbance measurement cell (light path 1 cm) kept at 37° C., and absorbance is measured over a period of 5 minutes (if necessary, over a longer period of time) at intervals of one minute at a wavelength of 340 nm. A quantity of enzyme capable of forming 1 micromole of NADH in one minute is taken as one unit. As above, the enzyme of this invention is a novel enzyme which is entirely hitherto unknown in action and substrate-specificity.

Next, the production process of the novel N-AMDH according to the present invention will be explained.

The microbial strain used belongs to Genus Flavobacterium and has an N-AMDH-producing ability. One concrete example of such strain is Flavobacterium sp. No. 141-8; and varieties and mutant strains thereof are also usable. Flavobacterium sp. No. 141-8 is a strain which has been isolated by the present inventors first from the soil, and its bacteriological properties are as follows.

(a) Morphology

Microscopic observation (cultured in sugar-bouillon medium at 30° C. for 16 hours)
(1) Size of cell: Rod having a size of 0.45–0.5×0.5–11 microns.
(2) Polymorphism of the cell: The shape ranges from a nearly spherical form to longer rod-like form, with contamination by short chain-like conjunction at terminals.
(3) Motility: Non-motile.
(4) Spore: None.
(5) Gram-stain: Negative.
(6) Acid-fast: Negative.

(b) State of Growth in Various Media
(1) Bouillon-agar plate culture (2 days at 30° C.)
Circular colonies are smooth and translucent; 0.5 mm diameter; relatively bad growth.
(2) Sugar-bouillon-agar plate culture (2 days at 30° C.)
Circular colonies are smooth and translucent; 0.8 mm in diameter; milky white mucous colonies are formed in 5 days; no pigment produced.
(3) Sugar-bouillon-agar slant culture (2 days at 30° C.)
Milky turbid mucous liquid; in 3 days, the liquid flows down and gathers at bottom.
(4) Sugar-bouillon liquid culture (2 days at 30° C.)
A slight growth
(5) Bouillon-gelatin stab culture (3 days at 30° C.)
A slight growth without liquefaction.
(6) Litmus milk: No change, nor coagulation.

(c) Physiological Properties
(1) Reduction of nitrates: Positive.
(2) Denitrification: Negative.
(3) MR test: Negative, provided that positive in aerobic culture.
(4) VP test: Negative.
(5) Formation of indole: Negative.

(6) Formation of hydrogen sulfide Negative.
(7) Hydrolysis of starch: Negative
(8) Utilization of citric acid: Negative.
(9) Utilization of inorganic nitrogen source: Ammonia is utilized, while nitric acid is not utilized.
(10) Formation of pigment: Negative.
(11) Urease: Positive.
(12) Oxidase: Positive.
(13) Catalase: Positive.
(14) Growing condition range: 15° C.–41° C. (optimum temperature 30° C.), pH 4.5–8.5 (optimum pH ca. 6.5)
(15) Behavior to oxygen: aerobic; a slight growth under anaerobic condition, too.
(16) O-F test: No change, or a very weak fermentation.
(17) Formation of acid and gas from sugars: * means aerobic culture:

*Formation of acid Formation of gas

|         |             | *Formation of acid | Formation of gas |
|---------|-------------|--------------------|------------------|
| (i)     | L-Arabinose | +                  | −                |
| (ii)    | D-Xylose    | +                  | −                |
| (iii)   | D-Glucose   | +                  | −                |
| (iv)    | D-Mannose   | +                  | −                |
| (v)     | D-Fructose  | +                  | −                |
| (vi)    | D-Galactose | +                  | −                |
| (vii)   | Maltose     | +                  | −                |
| (viii)  | Sucrose     | +                  | −                |
| (ix)    | Lactose     | +                  | −                |
| (x)     | Trehalose   | +                  | −                |
| (xi)    | D-Sorbit    | +                  | −                |
| (xii)   | D-Mannit    | +                  | −                |
| (xiii)  | Inosit      | +                  | −                |
| (xiv)   | Glycerin    | +                  | −                |
| (xv)    | Starch      | −                  | −                |

(d) Other Characteristics (1) Penicillin resistance: Growth even at 100 units/ml.
(2) Sodium chloride resistance: No growth above 2%.
(3) Motility of colony rim: No fluidity observed.
(4) Decomposition of Tween 80: Negative.
(5) Decomposition of esculin: Negative.

By comparing the above-mentioned characteristic properties of the above-mentioned novel N-AMDH-producing strain with the classification mentioned in "Bergey's Mannual of Systematic Bacteriology (1984) Vol. 1", it is considered that this strain belongs to Genus Flavobacterium because it is a gram-negative, aerobic, non-sporeforming bacillus having no motility, and it is catalase-positive and oxidase-positive and forms acid from many sugars under aerobic conditions, and it is resistant to Penicillin.

Since it forms acid from sugars under aerobic conditions, it is considered analogous to Flavobacterium spiritivorum. However, it is different from the latter in the decomposition of esculin, reduction of nitrate and decomposition of Tween 80. Thus, it can be regarded as a novel strain unknown so far.

For the reasons mentioned above, this strain has been named Flavobacterium sp. No. 141-8. Flavobacterium sp. No. 141-8 has been deposited in Fermentation Research Institute, Agency of Industrial Science and Technology, Ministry of International Trade and Industry, Japan, as FERM BP-1222 under the Budapest Treaty on the International Recognition of the Deposit of Microorganisms for the Purpose of Patent Procedure.

The medium used in the present invention may be any of synthetic and natural media, so far as it appropriately contains carbon source, nitrogen source, inorganics and other nutrients. As the carbon source, glucose, galactose, fructose, xylose, glycerin and the like can be used. As the nitrogen source, not only ammonium salts but also nitrogen-containing organic compounds such as peptone, digested casein, sodium glutaminate, yeast extract and the like are successfully usable. As the inorganics, salts of sodium, potassium, magnesium, manganese, calcium, iron and the like can be used.

In the present invention, N-AMDH is obtained in a high yield when a strain having N-AMDH-producing ability is cultured or dipped in a medium containing N-AM or N-acetylglucosamine. As a preferable example of said medium, a medium comprising 0.5% of N-AM, 0.1% of meat extract, 0.5% of polypeptone, 0.2% of yeast extract, 0.14% of sodium chloride and 0.1% of monopotassium hydrogen phosphate and having a pH value of 6.8 can be referred to. When the strain is subjected to aeration-agitation culture in this medium at 30° C. for 36 hours, the production titer is 10 to 100 times as high as that obtained in a culture using other carbon source in place of N-AM.

Temperature of the culture is usually 20° to 40° C. and preferably 30° to 33° C. Starting pH of the culture is usually 6 to 8 and preferably about 7. Under such conditions, a shaking culture or a submerged agitation culture is carried out for 20 to 40 hours. Otherwise, the bacterial cells which have been grown in other medium suitable for its growth and not containing A-AM or N-acetylglucosamine are dispersed in the above-mentioned medium at a high concentration aerobically for 1–10 hours in the presence of N-AM and N-acetylglucosamine. Thus, N-AMDH is accumulated in the cultured product or cell suspension.

Since N-AMDH is usually present in bacterial cells, it is preferable to separate bacterial cells by centrifugation or filtration. By disrupting the cells in an appropriate amount of buffer, the enzyme is solubilized and released into the solution.

As the means for disrupting bacterial cells, physical means such as Dynomill, French press, ultrasonic wave and the like, chemical means such as Triton X-100, sodium lauryl sulfate, EDTA and the like, or enzymatic means such as lysozyme and the like is used either alone or in combination. After disrupting bacterial cells, nucleic acid is removed in the usual manner and insoluble matter is removed by filtration or centrifugation, whereby N-AMDH is obtained.

If desired, N-AMDH thus obtained is further purified according to the conventional means for isolation and purification of enzymes such as (1) column chromatography using DEAE-cellulose column, (2) fractionating precipitation using ammonium sulfate, (3) column chromatography using DEAE-Sephadex column, (4) column chromatography using 5'-AMP-Sepharose column, (5) gel filtration using Sephadex, and the like, or their appropriate combination, whereby a purified N-AMDH can be obtained.

Next, the method for quantitatively analyzing N-AM or SA and the quantative analysis kit of the present invention will be concretely illustrated.

The principle of the measurement of the invention is as shown below:

That is, N-AMDH is reacted with N-AM in a sample, and the formed NADH is measured according to well known method of measurement, such as measurement of absorbance at 340 nm (ultraviolet region).

Otherwise, it is also possible to measure the formed NADH by contacting sample with various enzymes fixed on a solid. If necessary for preventing the influence of coexisting LDH, an inhibitor such as oxamic acid, oxalic acid or the like may be added in an appropriate amount.

The N-AMDH used in the invention may be of any origin. Preferably, the N-AMDH obtained by culturing a microorganism, particularly a strain selected from the bacteria belonging to Genus Flavobacterium, is used.

As the above-mentioned enzyme-producing strain belonging to Genus Flavobacterium, Flavobacterium sp. No. 141-8 (FERM BP-1222) can be referred to, for example.

In reacting N-AMDH with N-AM in a sample, the reaction is carried out at a pH value of 7-10 at a temperature of 50° C. or below, preferably at a pH value of 8-9.5 at a temperature of 30°-45° C., and usually for a period of about 2 to 20 minutes. For regulating pH value, any buffer solution may be used, so far as it can maintain the above-mentioned pH range and does not disturb the enzymatic reaction. For example, potassium phosphate buffer, tris-hydrochloric acid buffer, glycine-sodium hydroxide buffer, sodium carbonate buffer and the like are successfully usable for this purpose.

Though the quantitative analysis of NADH formed by the action of N-AMDH may be carried out by any methods, the most generally used method is measurement of absorbance at 340 nm (ultraviolet region). Apart from above, there are a few methods which comprise converting NADH into a dye having absorption in the visible region and then determining the dye, such as the method which comprises reacting NADH with phenazine methosulfate and Nitrobluetetrazolium and measuring the absorption of the resulting diformazan at 570 nm, and the method which comprises reacting NADH with NADH-oxidase (J. Biochem. 98, 1433 (1985)), phenazine methosulfate or an electron transferring substance or metallic ion exhibiting a similar behavior to form hydrogen peroxide, developing a color therefrom in the presence of peroxidase and various chromogens, and measuring absorbance at appropriate wavelengths. When NADH is derived into hydrogen peroxide, it is also possible to analyze it by developing a luminescence from it in the presence of luminol. It is also possible to analyze NADH semi-quantitatively by adding appropriately selected plural redox indicators and electron transferring substances and observing the color tone. All these method of detection may be selected in accordance with their characteristic features.

In quantitatively analyzing SA, an SA-containing sample is reacted with N-acetylneuraminic acid aldolase to decompose SA into N-AM and pyruvic acid, followed by treating the decomposant solution with N-AMDH and making measurement in the same manner as above.

In analyzing SA, the SA in a sample must be in the liberated state. When SA is combined with protein or glycolipid as in serum, plasma and some tissues, the SA is once liberated by the action of neuraminidase and then analyzed. Though the neuraminidase used in this case may be of any origin, those produced by microorganisms belonging to Genus Clostridium, Genus Arthrobacter, Genus Corynebacterium, Genus Streptococcus, etc. are preferable.

Next, the kit of the invention for quantative analysis of N-AM or SA is composed of N-AMDH or N-AMDH and N-acetylneuraminic acid aldolase, NAD, enzymes and reagents for quantatively analyzing the formed NADH, and buffering reagent for smoothly advancing the reaction. These reagents and enzymes are used in the form of liquid, solid or freeze-dried material, and they are dissolved and mixed into buffer solution before use in accordance with requirement to make a measuring reagent.

In determining N-AM, the kit is directly acted upon N-AM-containing sample to form NADH. The NADH is measured either directly or after addition of NADH-analyzing reagents.

In determining SA, N-acetylneuraminic acid aldolase is firstly reacted upon sample to form N-AM. Next, N-AMDH is reacted to form NADH. The NADH is determined either directly or after addition of NADH-measuring reagents. The system for the measurement may be any of single reagent system, double reagent system and multi reagent system.

When the novel N-AMDH of the present invention is used, N-AM can be quantitatively analyzed with a high accuracy and based on it the quantity of SA can be known. As its result, various diseases can be diagnosed effectively. Further, according to the invention, N-AM can be exactly analyzed quantitatively without influence of coexisting N-acetylhexosamine, which is quite meaningful in the studies of complex sugars. Similarly, the present invention enables to quantitatively analyze SA with a high exactness without influence of endogenous pyruvic acid, which is quite meaningful in the diagnosis based on clinical tests of SA.

Next, the present invention will be illustrated with reference to the Examples.

EXAMPLE 1

A 300 ml Erlenmeyer flask containing 50 ml of a seed culture medium (pH 8.0) containing 0.75% of glucose, 0.2% of yeast extract, 0.5% of polypeptone, 0.1% of meat extract, 0.14% of sodium chloride and 0.1% of monopotassium hydrogen phosphate was inoculated with Flavobacterium sp. No. 141-8 (FERM BP-1222). After a shaking culture at 30° C. for 24 hours, the seed culture fluid was transplanted into a jar fermenter (manufactured by Iwashiya Seibutsu Kagaku K. K.) containing 2 liters of the same medium as above and subjected to an aeration (2 liters/minute) agitation (400 rpm) culture at 30° C. for 36 hours. The culture fluid was centrifuged at 8,000 rpm for 20 minutes to collect the bacterial cells.

The cells were transferred into the same jar fermenter as above containing 2 liters of a medium containing 0.2% of N-AM, 0.1% of meat extract, 0.5% of polypeptone, 0.2% of yeast extract, 0.14% of sodium chloride and 0.1% of monopotassium hydrogen phosphate and having a pH value of 6.8, and culture was continued under the same conditions as above. Six hours after, activity of N-AMDH reached the maximum.

To 1.7 kg of live bacterial cell obtained, 10 liters of 0.02M tris-hydrochloric acid buffer (pH 8.0, hereinafter this is referred to as "standard buffer") was added, and then Triton X-100 and EDTA were added so that their concentration came to 0.5% and 2 mM, respectively. The mixture was stirred overnight in a cold room to obtain a uniform suspension. It was milled by means of Dynomill (manufactured by SHINMARU Enterprise Co., Sweden) at 3,000 rpm and centrifuged at 8,000 rpm for 20 minutes to obtain 7.3 liters of a supernatant liquid.

Then, 1.4 kg of DEAE-cellulose in wetness was added to the supernatant liquid, and the mixture was adjusted to pH 8.0 and stirred for 30 minutes to have the enzyme adsorbed on the DEAE-cellulose. After transferring it to a Buchner funnel and filtering it, it was washed with 4 liters of standard buffer and then with 5 liters of standard buffer containing 0.3M of sodium chloride. The fractions eluted with the last washing were combined and concentrated to one liter by means of hollow fiber ultrafiltrater (manufactured by Asahi Kasei Kogyo K. K.).

Into the concentrate was added and dissolved 125 g of ammonium sulfate. After thoroughly stirring the mixture and allowing it to stand for 2 hours, it was centrifuged at 9,000 rpm for 20 minutes to obtain 850 ml of supernatant liquid. After adding an additional 166 g of ammonium sulfate and thoroughly dissolving it, the mixture was left standing overnight in a cold room.

Then it was centrifuged at 12,000 rpm for 20 minutes to collect the resulting precipitate, and the latter was dissolved into 850 ml of standard buffer. After dissolving 35 g of ammonium sulfate thereinto, the resulting solution was passed through a column (5 cm in diameter and 34 cm in height) of Phenyl-Sepharose CL-4B (manufactured by Pharmacia Fine Chemicals, Sweden) previously equilibrated with standard buffer containing 4% of ammonium sulfate to have the enzyme adsorbed on the column. The enzyme was eluted with 10 liters of standard buffer having a concentration gradient of ethylene glycol (0 to 30%) and a reverse concentration gradient of ammonium sulfate (4 to 0%) at the same time.

The eluate was concentrated by ultrafiltration and dialyzed against standard buffer containing 0.1M sodium chloride. Then it was passed through a DEAE-Sephadex A-50 column (5 cm in diameter and 52 cm in height) previously equilibrated with standard buffer containing 0.1M sodium chloride for the sake of adsorption, and then the adsorbed matter was eluted with 10 liters of standard buffer having a sodium chloride concentration gradient ranging from 0.1M to 0.28M.

The active fraction was concentrated by ultrafiltration and then dialyzed against 0.01M potassium phosphate buffer (pH 6.5). Then it was passed through a column (4 cm in diameter and 16 cm in height) of 5'-AMP-Sepharose CL-4B (manufactured by Pharmacia Fine Chemicals, Sweden) previously equilibrated with 0.01M potassium phosphate buffer (pH 6.0) for the sake of adsorption, and the adsorbed matter was eluted with a buffer having sodium chloride concentration gradient (0–0.5M) and pH gradient (6.0–8.0) at the same time, by the use of 4 liters of 0.01M phosphate buffer (pH 6.0) and 4 liters of 0.01M phosphate buffer containing 0.5M sodium chloride (pH 8.0).

The active fraction was adjusted to pH 8.0 and then concentrated to 1 ml by means of ultra filter and collodion bag concentration apparatus, and the concentrate was dialyzed against standard buffer containing 0.1M sodium chloride. The dialyzed solution was subjected to gel filtration through a Sephadex G-200 column (2.5 cm in diameter and 95 cm in height) previously equilibrated with standard buffer containing 0.1M sodium chloride.

The active fractions were combined and concentrated to obtain 2200 units of purified N-AMDH. As shown in FIG. 5, it was an enzyme sample exhibiting a nearly single band in disk electrophoresis.

EXAMPLE 2

In the same manner as in Example 1, Flavobacterium sp. No. 141-8 was transplanted into 50 ml of a seed culture medium (pH 6.8) containing 0.5% of N-AM, 0.8% of polypeptone, 0.1% of meat extract, 0.2% of yeast extract and monopotassium hydrogen phosphate and subjected to a shaking culture at 30° C. for 24 hours.

The culture fluid was transplanted into a miniature jar fermenter containing the same medium as above, and subjected to aeration (2 liters/minute) agitation (400 rpm) culture at 30° C. for 40 hours. N-AMDH was accumulated in the bacterial cells. The bacterial cells thus obtained were treated in the same manner as in Example 1 to obtain an N-AMDH sample.

EXAMPLE 3

Concentration of N-AM in the solution was determined with the following reagents.

1. Reagents

| | |
|---|---|
| 0.1M phosphate buffer (pH 8.0) | 880 microliters |
| NAD (60 mM) | 50 microliters |
| N-AMDH (123 units/ml) | 30 microliters |
| Sample solution | 20 microliters |

2. Method of determination

Figure 6:
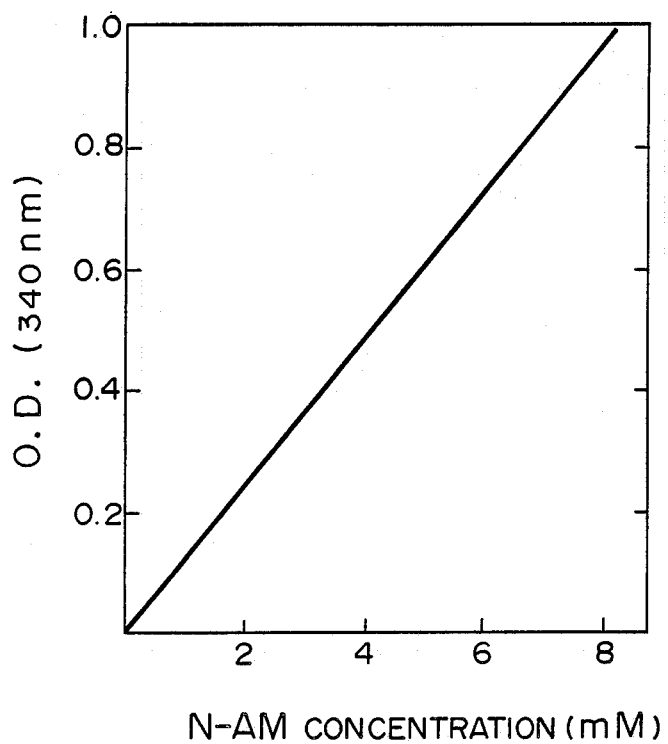
FIG. 6 is calibration curve in Example 3.

Predetermined quantities of the reagents were taken into a test tube and reacted at 37° C. for 10 minutes, after which absorbance was measured at 340 nm. In a blank test, the above-mentioned procedure was repeated, except that the sample solution was replaced with an identical quantity of water. Absorbance of the blank run was subtracted from that of the sample run, and the remainder was taken as absorbance of sample solution. Apart from above, N-AM solutions having known concentrations were treated in the same manner as above, from which a calibration curve was prepared. From the calibration curve, a concentration of N-AM in unknown sample was determined. FIG. 6 is the calibration curve.

EXAMPLE 4

Concentration of N-AM in solution was determined by the following method by the use of the following reagents.

1. Reagents

| | |
|---|---|
| 0.1M Phosphate buffer (pH 8.0) (containing 0.1% Triton X-100) | 140 microliters |
| Phenazine methosulfate (1 mg/ml) | 5 microliters |
| Nitroblue tetrazolium (10 mg/ml) | 5 microliters |
| NAD (40 mg/ml) | 20 microliters |
| N-AMDH (123 units/ml) | 10 microliters |
| Sample solution | 10 microliters |

2. Method of determination

Predetermined quantities of the above-mentioned reagents were taken into a test tube and reacted at 37° C. for 15 minutes. Then, 2.0 ml of 0.3N hydrochloric acid was added and thoroughly stirred. Absorbance of the formed color was measured at 570 nm. In a blank test, the reaction was repeated, except that the sample solution was replaced with identical quantity of water. Absorbance of blank solution was subtracted from that of the sample solution, and the remainder was taken as absorbance of sample. Apart from above, a calibration curve was prepared from solutions having known N-AM concentrations. From the calibration curve, N-AM concentration in sample solution was determined.

EXAMPLE 5

Quantity of SA in serum was determined by the following procedure with the following reagents.

1. Reagents

| | | |
|---|---|---|
| A. | 10 mM Phosphate buffer (pH 6.6) | 1 ml |
| | Neuraminidase (5 units/ml) | 1 ml |
| | N-Acetylneuraminic acid aldolase (10 units/ml) | 1 ml |
| B. | 0.1 M Phosphate buffer (pH 8.0) | 5.7 ml |
| | N-AMDH (123 units/ml) | 0.6 ml |
| | NAD (60 mM) | 0.5 ml |
| | Oxamic acid | 4.4 mg |

2. Method of determination

Twenty microliters of serum was taken into a test tube, to which was added 300 microliters of reagent A. After reacting them at 37° C. for 15 minutes, 680 microliters of reagent B was added and reacted for an additional 10 minutes. Absorbance of the reaction mixture was measured at 340 nm. In blank test, the above-mentioned procedure was repeated except that reagent A was replaced with water. Absorbance of blank run was subtracted from that of the sample run. A calibration curve was prepared from solutions containing known concentrations of N-acetylneuraminyllactose. From the calibration curve, SA concentration in sample was determined.

EXAMPLE 6

Activity of N-acylglucosamine-2-epimerase extracted from hog kidney was determined by the following procedure with the following reagents.

1. Reagents

| | | |
|---|---|---|
| A. | 0.5M Tris-hydrochloric acid buffer (pH 7.4) | 25 microliters |
| | 0.1M MgCl$_2$ | 25 microliters |
| | 0.1M Acetylglucosamine | 100 microliters |
| | 0.1M ATP (adjusted to pH 7.6) | 10 microliters |
| B. | 0.1M Tris-hydrochloric acid buffer (pH 8.2) | 700 microliters |
| | N-AMDH (123 units/ml) | 30 microliters |
| | NAD (60 mM) | 100 microliters |

2. Method of Determination

An enzyme solution extracted from hog kidney (Biochemistry, 9, 3363) was dissolved into 20 mM potassium phosphate buffer (pH 7.6), and 10 microliters of the resulting solution was reacted with reagent A at 37° C. for 20 minutes. It was heated at 100° C. for 2 minutes and then cooled to 37° C., after which a predetermined amount of reagent B was added and reacted for 5 minutes. Absorbance of the reaction mixture was measured at 340 nm. In blank test, the above-mentioned procedure was repeated, except that the enzyme solution was replaced with water. Absorbance of the blank run was subtracted as control from that of sample run, and the remainder was taken as the increase of absorbance attributable to the formed N-AM. Based on the fact that 1 mM of N-AM corresponded to an absorbance of 6.27 in the reaction mixture, concentration of N-AM was calculated, and it was taken as the amount of N-AM formed during 20 minutes. By converting it into "formation per one hour" and multiplying the latter by 100, enzyme activity per 1 ml of enzyme solution was determined.

EXAMPLE 7

Concentration of SA in a solution was determined by the following procedure with the following reagents.

1. Reagents

| | |
|---|---|
| 0.1M Phosphate buffer (pH 8.0) | 610 microliters |
| N-Acetylneuraminic acid aldolase | 300 microliters |
| (manufactured by Nakarai Kagaku K. K.) | |
| (10 units/ml) | |
| NAD (60 mM) | 53 microliters |
| N-AMDH (123 units/ml) | 60 microliters |
| Sample solution | 20 microliters |

2. Method of determination

Figure 7:
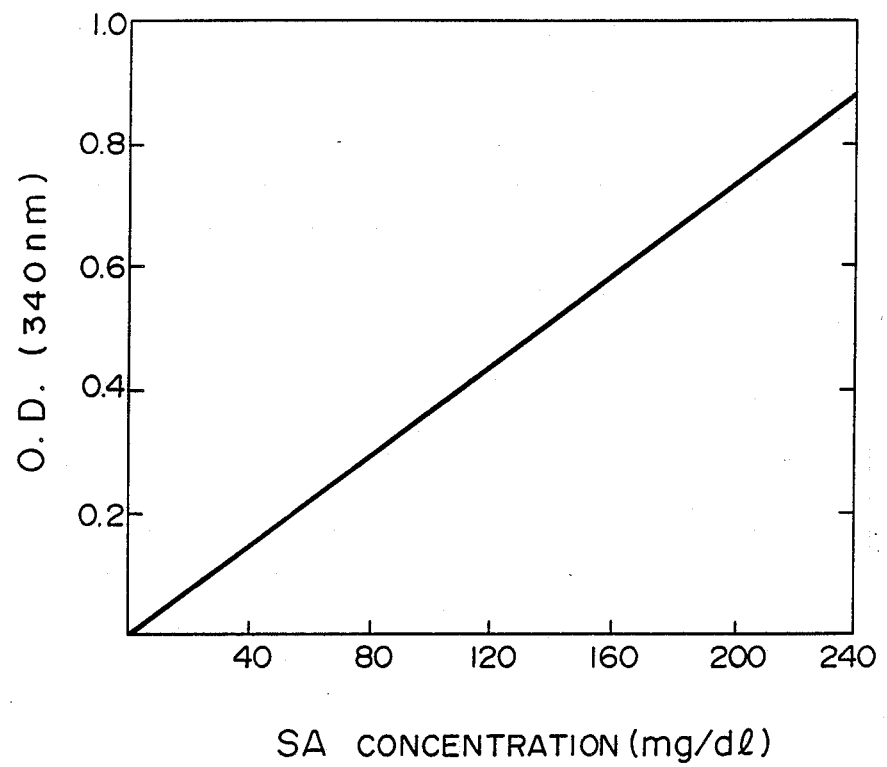
FIG. 7 is calibration curve in Example 7; provided that the buffer solutions used in FIG. 1 and FIG. 2 were potassium phosphate buffer (O-O), trishydrochloric acid buffer (Δ-Δ) and glycine-sodium hydroxide buffer (●-●).

Predetermined quantities of the reagents were taken into a test tube and reacted at 37° C. for 10 minutes, after which absorbance of the reaction mixture was measured at 340 nm. In blank test, the above-mentioned procedure was repeated, except that N-acetylneuraminic acid aldolase was replaced with identical quantity of water. Absorbance of the blank run was subtracted from that of sample run, and the remainder was taken as an absorbance of sample solution. Apart from the above, a calibration curve was prepared by treating SA solutions of known concentrations in the same manner as above. From the calibration curve, SA concentration in sample solution was determined. FIG. 7 is the calibration curve.

EXAMPLE 8

Concentration of SA in solution was determined by the following procedure with the following reagents.

1. Reagents

| | |
|---|---|
| 0.1M Phosphate buffer (pH 8.0) | 100 microliters |
| (containing 0.1% Triton X-100) | |
| Phenazine methosulfate (1 mg/ml) | 5 microliters |
| Nitroblue-tetrazolium (10 mg/ml) | 5 microliters |
| NAD (40 mg/ml) | 20 microliters |
| N-Acetylneuraminic acid aldolase | 40 microliters |
| (manufactured by Nakarai Kagaku K. K.) | |
| (10 units/ml) | |
| N-AMDH (123 units/ml) | 10 microliters |
| Sample solution | 10 microliters |

2. Method of determination

Predetermined quantities of the above-mentioned reagents were taken into a test tube and reacted at 37° C. for 15 minutes. After adding 2.0 ml of 0.3N hydrochloric acid, it was thoroughly stirred. Absorbance of the formed color was measured at 570 nm. In blank test, the above-mentioned treatment was repeated, except that N-acetylneuraminic acid aldolase was replaced with identical quantity of water. Absorbance of the blank run was subtracted as control from that of the sample run, and the remainder was taken as an absorbance of sample. Apart from above, a calibration curve was prepared by treating SA solutions of known concentrations in the same manner as above. From the calibration curve, SA concentration in sample solution was determined.

What is claimed is:

1. Purified N-acetylmannosamine dehydrogenase taking off hydrogen from N-acetylmannosamine to convert it into N-acetylmannosaminolactone and, at the same time, reducing coenzyme NAD into NADH, of which optimum pH is 8.0 to 9.0, of which stable pH range is 8.5 to 9.5, and of which molecular weight is 110,000 to 120,000 as measured by gel filtration method.

2. A process for producing N-acetylmannosamine dehydrogenase which comprises culturing a strain Flavobacterium sp. No. 141-8 (FERM BP-1222) having an ability to produce N-acetylmannosamine dehydrogenase in a culture medium and collecting N-acetylmannosamine dehydrogenase from the cultured product.

3. A process according to claim 2, wherein said cultured product is centrifuged or filtered to separate bacterial cells and the cells are disrupted in a buffer solution to solubilize the enzyme.

4. A process for producing the N-acetylmannosamine dehydrogenase which comprises culturing a strain Flavobacterium sp. No. 141-8 (FERM BP-1222) having an ability to produce N-acetylmannosamine dehydrogenase in a culture medium by a method of shaking culture or submerged agitation culture at a temperature of 20° C. to 40° C. for a period of 20 to 40 hours, and collecting N-acetylmannosamine dehydrogenase from the cultured product.

* * * * *